US006838434B2

(12) United States Patent
Voet

(10) Patent No.: US 6,838,434 B2
(45) Date of Patent: Jan. 4, 2005

(54) METHODS FOR TREATING SINUS HEADACHE

(75) Inventor: Martin A. Voet, San Juan Capistrano, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/429,069

(22) Filed: May 2, 2003

(65) Prior Publication Data

US 2004/0219172 A1 Nov. 4, 2004

(51) Int. Cl.$^7$ ............................................. A61K 38/00
(52) U.S. Cl. ........................................................ 514/2
(58) Field of Search .............................. 424/400; 514/2

(56) References Cited

U.S. PATENT DOCUMENTS

| | | | |
|---|---|---|---|
| 5,437,291 A | 8/1995 | Pasricha et al. |
| 5,670,484 A | 9/1997 | Binder |
| 5,674,205 A | 10/1997 | Pasricha et al. |
| 5,714,468 A | 2/1998 | Binder |
| 5,766,605 A | 6/1998 | Sanders et al. |
| 5,989,545 A | 11/1999 | Foster et al. |
| 6,063,768 A | 5/2000 | First |
| 6,113,915 A | 9/2000 | Aoki et al. |
| 6,139,845 A | 10/2000 | Donovan |
| 6,143,306 A | 11/2000 | Donovan |
| 6,265,379 B1 | 7/2001 | Donovan |
| 6,299,893 B1 | 10/2001 | Schwartz et al. |
| 6,306,403 B1 | 10/2001 | Donovan |
| 6,306,423 B1 | 10/2001 | Donovan et al. |
| 6,312,708 B1 | 11/2001 | Donovan |
| 6,328,977 B1 | 12/2001 | Donovan |
| 6,358,513 B1 | 3/2002 | Voet et al. |
| 6,365,164 B1 | 4/2002 | Schmidt |
| 6,395,277 B1 | 5/2002 | Graham |
| 6,423,319 B1 | 7/2002 | Brooks et al. |
| 6,429,189 B1 | 8/2002 | Borodic |
| 6,458,365 B1 | 10/2002 | Aoki et al. |
| 6,464,986 B1 | 10/2002 | Aoki et al. |
| 2002/0036943 A1 | 3/2002 | Fujimoto |
| 2002/0187164 A1 | 12/2002 | Borodic |
| 2002/0192239 A1 | 12/2002 | Borodic et al. |
| 2002/0197278 A1 | 12/2002 | Allison |
| 2002/0197279 A1 | 12/2002 | Aoki et al. |
| 2003/0143249 A1 * | 7/2003 | Lamb ....................... 424/239.1 |

OTHER PUBLICATIONS

Anderson, T. et al., Surgical Intervention for Sinusitis in Adults; *Current Allergy and Asthma Reports;* 2001, 1:282–288.

Aoki, K.R. et al., Botulinum toxin type A and other botulinum toxin serotypes: a comparative review of biochemical and pharmacological actions; *European Journal Neurology;* 2001; 8 (Suppl 5):pp 21–29.

Aoki, K.R.; Physiology and Pharmacology of Therapeutic Botulinum Neurotoxins; In: Kreyden OP, ed. *Hyperhidrosis and Botulinum Toxin in Dermatology;* Current Problems in Dermatology; Basel, Karger; 2002; 30: pp. 107–116.

Bigalke, Hans et al., Botulinum A Neurotoxin Inhibits Non–Cholinergic Synaptic Transmission in Mouse Spinal Cord Neurons in Culture; *Brain Res;* 1985; 360: pp 381–24.

Bigalke, H. et al., Tetanus Toxin and Botulinum A Toxin Inhibit Release and Uptake of Various Transmitters, as Studied with Particulate Preparations from Rat Brain and Spinal Cord; *Naunyn Schmiedebergs Arch Pharmacol;* 1981; 316; pp 244–51.

Binz, Thomas et al., The Complete Sequence of Botulinum Neurotoxin Type A and Comparison with Other Clostridial Neurotoxins; *J Biochem;* (Tokyo) Jun. 5, 1990; 265(16); pp 9153–8.

Borodic, et al., Management of facial pain with botulinum toxin in a tertiary pain clinic, *Naunyn Schmiedebergs Arch Pharmacol,* 2002;365(Suppl 2):R14.

Brem, Henry et al., Placebo–controlled trial of safety and efficacy of intraoperative controlled delivery by biodegradable polymers of chemotherapy for recurrent gliomas; *The Lancet;*vol. 345; Apr. 22, 1995; pp 1008–1012.

Brin, Mitchell F. et al., Botulinum Toxin Type A: Pharmacology; In: Mayer Nathaniel H, ed. *Spasticity: Etiology, Evaluation, Management and the Role of Botulinum Toxin;* 2002; pp 110–124.

Bushara, K.O., Botulinum Toxin and Rhinorrhea; *Otolaryngol Head Neck Surg;* 1996; 114(3): 507.

Cui, M. et al., Mechanisms of the Antinociceptive Effect of Subcutanous Botox®: Inhibition of Peripheral and Central Nociceptive Processing; *Naunyn Schmiedebergs Arch Pharmacol;* 2002; 365 (Suppl 2) R17; Abstract.

Moyer, Elizabeth et al., Botulinum Toxin Type B: Experimental and Clinical Experience; In: Jankovic J, ed. *Neurological Disease and Therapy. Therapy with botulinum toxin;* 1994; 25; pp 71–85.

Naumann, Markus et al., Botulinum toxin type A in the treatment of focal, axillary and palmar hyperhidrosis and other hyperhidrotic conditions; *European Journal of Neurology;* 1999, vol. 6 (suppl 4) pp S111–5.

Pearce, Bruce et al., Pharmacologic Characterization of Botulinum toxin for Basic Science and Medicine; *Toxicon;* 1997; 35(9); pp 1373–412.

Ragona, Rosario M. et al., Management of Parotid Sialocele With Boutulinum Toxin; *Laryngoscope;* 109; Aug. 1999 (8); pp 1344–1346.

Rollnik, J.D., et al., Botulinum Toxin (DYSPORT) in Tension–type headaches, *Acta Neurochir,* 2002;79(Suppl):123–126.

(List continued on next page.)

Primary Examiner—Alton N. Pryor
(74) Attorney, Agent, or Firm—Stephen Donovan

(57) ABSTRACT

A sinus headache can be treated by administration of a *botulinum* toxin to a patient. The *botulinum* toxin can be *botulinum* toxin type A and the *botulinum* toxin can be administered to or to the vicinity of a sinus membrane of a patient with a sinus headache.

20 Claims, 3 Drawing Sheets

OTHER PUBLICATIONS

Rohrbach, S., et al., Minimally invasive application of botulinum toxin type A in nasal hypersecretion, *J Oto–Rhino–Laryngol* 2001, Nov.–Dec.;63(6):382–4.

Sanchez–Prieto, Jose et al., Botulinum toxin A blocks glutamate exocytosis from guinea–pig cerebral cortical synaptosomes; *Eur J Biochem;* Jun. 1987; 165 (3); pp 675–81.

Schantz, Edward J. et al., Properties and Use of Boulinum Toxin and Other Microbial Neurotoxins in Medicine; *Microbiol Review;* Mar. 1992; 56 (1); pp 80–99.

Singh, Bal Ram; Critical Aspects of Bacterial Protein Toxins; *Natural Toxins II;* Edited by B. R. Singh et al., Plenum Press, New Yrok, 1996; Chapter 4, pp 63–84.

Sloop, R. et al., Reconstituted botulinum toxin type A does not lose potency in humans if it is refrozen or refrigerated for 2 weeks before use; *Neurology;* Jan. 1997; 48(1): 249–53.

Thant, Z–S., et al., Emerging therapeutic applications of botulinum toxin, *Med Sci Monit* 2003, Janj;9(2):RA40–RA48.

Wiegand, H. et al., I–Labelled Botulinum A Neurotoxin: Pharmacokinetics in Cats after intramuscular Injection; *Naunyn Schmiedebergs Arch Pharmacol;* 1976; 292; pp 161–5.

PDF file from website www.imigaine.net/patient/guide.pdf on Mar. 13, 2003, *Wake Forest University Baptist Med Center, Dept. of Neurology;* Headache: A Patient's Guide, 15 pgs.

Duggan, Michael J. et al., A survey of botulinum neurotoxin substrate expression in cells; *Mov Disord;* May 1995; 10(3) p. 376.

Evers, S., et al., Treatment of headache with botulinum toxin A—a review according to evidence–based medicine criteria, *Cephalalgia* 2002, Nov.;22(9): 699–710.

Fauci et al., *Harrison's Principles of Internal Medicine; 14th* ed.

Ferrari, David M. et al., The protein disulphide–isomerase family: unravelling a string of folds; *Biochem J;* 1999 (339) pp 1–10.

Freund, B.J., et al. The use of botulinum toxin–A in the treatment of refractory cluster headache: case reports, *Cephalagia* 2000;20(4):329–330, p. 159.

Freund, B.J., et al., Relief of tension–type headache symptoms in subjects with tempooromandibular disorders treated with botulinum toxin–A, *Headache* 2002 Nov.–Dec.; 42(10):1033–1037.

Freund, B.J., Treatment of Chronic Cervical—Associated headache with botulinum toxin A: a pilot study, *Headache 2000,* Mar.; 40(3):231–236.

Fung, Lawrence K. et al., Pharmacokinetics of Interstitial Delivery of Carmustine, 4–Hydroperoxycyclophosphamide, and Paclitaxel from a Biodegradable Polymer implant in the Monkey Brain; *Cancer Research;* 58, Feb. 15, 1998; pp 672–684.

Guyton, Arthur C. et al., *Textbook of Medical Physiology 9th ed;* W.B. Saunders Company; pp 686–688.

Habermann, E., I–Labeled Neurotoxin from Clostridium Botulinum A: Preparation, Binding to Synaptosomes and Ascent to the Spinal Cord; *Naunyn Schmiedeberg's Arch. Pharmacol;* 1974; (281); pp 47–56.

Habermann, E., Inhibition by tetanus and botulinum A toxin of the release of {3H}noradrenaline and {3H} GABA from rat brain homogenate; *Experientia;* Mar. 15, 1988; 44(3) pp 224–6.

Habermann, E. et al., Tetanus Toxin and Botulinum A and C Neurotoxins Inhibit Noradrenaline Release from Cultured Mouse Brain; *J Neurochem;* vol. 51 No. 2 1988; pp 522–7.

Loder, E., et al., Use of botulinum toxins for chronic headaches: a focused review, *Clin J Pain* 2002; 18 (6 Suppl): S169–S176.

Jankovic, Joseph et al., *Therapy with Botulinum Toxin;* Marcel Dekker, Inc.; pp 5 and 150.

Marjama–Lyons, J. et al., Tremor–Predominant parkinson's Disease; *Drugs & Aging;* Apr. 16, 2000; (4); 273–278.

Mathew, N.T., et al., The use of botulinum toxin type A in headache treatment, *Curr Treat Options Neurol* 2002 Sep.;4(5):365–373.

\* cited by examiner

METHODS FOR TREATING SINUS HEADACHE

BACKGROUND

The present invention relates to methods for treating sinus headache. In particular, the present invention relates to methods for treating a sinus headache with a *botulinum* toxin.

Headache

A headache is a pain in the head, such as in the scalp, face, is forehead or neck. A headache can be a primary headache or a secondary headache. A primary headache is a headache which is not caused by another condition. Contrarily, a secondary headache is due to a disease or medical condition, such as an illness, infection, injury, stroke or other abnormality. Thus, with a secondary headache there is an underlying disorder that produces the headache as a symptom of that underlying disorder. Tension headache is the most common type of primary headache and tension headaches account for about 90% of all headaches. A tension headache is often experienced in the forehead, in the back of the head and neck, or in both regions. It has been described as a tight feeling, as if the head were in a vise. Soreness in the shoulders or neck is common. Nausea is uncommon with a tension headache.

About 2% of all headaches are secondary headaches. For example, a cervicogenic headache is a headache which is due to a neck problem, such as an abnormality of neck muscles, which can result from prolonged poor posture, arthritis, injuries of the upper spine, or from a cervical spine disorder.

Sinus headache is another type of secondary headache. A sinus headache can be caused by inflammation and/or infection in the paranasal sinuses. The paranasal sinuses are four pairs of hollow spaces or cavities (normally air filled) located within the skull or bones of the head surrounding the nose. The paranasal sinuses are the frontal sinuses over the eyes in the brow area, the maxillary sinuses inside each cheekbone, the ethmoid sinuses just behind the bridge of the nose and between the eyes and the sphenoid sinuses behind the ethmoid sinuses in the upper region of the nose and behind the eyes. Each of the paranasal sinuses has an opening into the nose for the free exchange of air and mucus, and each is joined with the nasal passages by a continuous mucous membrane lining. Therefore, anything that causes a swelling in the nose, such as an infection, an allergic reaction, or an immune reaction can also affect the sinuses. Air trapped within a blocked sinus, along with pus or other secretions, can cause pressure on the sinus wall. The result can be the pain of a sinus headache. Similarly, when air is prevented from entering a paranasal sinus by a swollen membrane at the opening, a partial vacuum can be created that can also result in sinus headache. Thus, a sinus headache can occur in the front of the face, usually around the eyes, across the cheeks, or over the forehead. The pain of a sinus headache is usually mild in the morning and increases in intensity during the day.

The pain of a sinus headache can be due to pressure within the sinuses cavities and the pain is typically localized over the involved sinus area, and is typically a constant, even, nonthrobbing pain. Usually a sinus headache is not associated with nausea, light, or noise sensitivity. If a sinus headache is accompanied by fever and/o a nasal discharge, then sinusitis is also indicated. Thus, a sinus headache can be secondary to sinusitis which is an inflammation of the sinus membranes that can be infectious (caused by a virus or bacteria) or non-infectious (often caused by allergies).

It is important to note that the sinuses are anatomically distinct from the nasal passages (i.e. the nasal vestibule, turbinate, or nasal meatus passages), due for example to the small, narrow and often occluded opening of the sinus cavities into the respective nasal passage, as shown by FIGS. 1–3.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a $LD_{50}$ in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated $LD_{50}$ of *botulinum* toxin type A of 0.3 ng equals 1 U is corrected for the fact that about 0.05 ng of BOTOX® equals 1 unit). One unit (U) of *botulinum* toxin is defined as the $LD_{50}$ upon intraperitoneal injection into female Swiss Webster mice weighing 18 to 20 grams each.

[1] Available from Allergan, Inc., of Irvine, Calif. under the tradename BOTOX® in 100 unit vials)

Seven generally immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. Moyer E et al., *Botulinum Toxin Type B: Experimental and Clinical Experience*, being chapter 6, pages 71–85 of "Therapy With Botulinum Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or. stages. In the first step of the process, the toxin binds to the presynaptic membrane of the target neuron through a specific interaction between the heavy chain, H chain, and a cell surface receptor; the receptor is thought to be different for each type of *botulinum* toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be-mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype $C_1$ was originally thought to cleave syntaxin, but was found to cleave syntaxin and SNAP-25. Each of the *botulinum* toxins specifically cleaves a different bond, except *botulinum* toxin type B (and tetanus toxin) which cleave the same bond. Each of these cleavages block the process of vesicle-membrane docking, thereby preventing exocytosis of vesicle content.

*Botulinum* toxins have been used in clinical settings for the treatment of neuromuscular disorders characterized by hyperactive skeletal muscles (i.e. motor disorders). In 1989 a *botulinum* toxin type A complex has been approved by the U.S. Food and Drug Administration for the treatment of blepharospasm, strabismus and hemifacial spasm. Subsequently, a *botulinum* toxin type A was also approved by the FDA for the treatment of cervical dystonia and for the treatment of glabellar lines, and a *botulinum* toxin type B was approved for the treatment of cervical dystonia. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months, although significantly longer periods of therapeutic activity have been reported.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type $C_1$ has been shown to cleave both syntaxin and SNAP-25. These differences in mechanism of action may affect the relative potency and/or duration of action of the various *botulinum* toxin serotypes. Apparently, a substrate for a *botulinum* toxin can be found in a variety of different cell types. See e.g. *Biochem J* 1;339 (pt 1):159–65:1999, and *Mov Disord*, 10(3):376:1995 (pancreatic islet B cells contains at least SNAP25 and synaptobrevin).

The molecular weight of the *botulinum* toxin protein molecule, for all seven of the known *botulinum* toxin serotypes, is about 150 kD. Interestingly, the *botulinum* toxins are released by *Clostridial bacterium* as complexes comprising the 150 kD *botulinum* toxin protein molecule along with associated non-toxin proteins. Thus, the *botulinum* toxin type A complex can be produced by *Clostridial bacterium* as 900 kD, 500 kD and 300 kD forms. *Botulinum* toxin types B and C, is apparently produced as only a 700 kD or 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522–527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675–681:1897. Thus, when adequate concentrations are used, stimulus-evoked release of most neurotransmitters is blocked by *botulinum* toxin. See e.g. Pearce, L. B., *Pharmacologic Characterization of Botulinum Toxin For Basic Science and Medicine*, Toxicon 35(9);1373–1412 at 1393; Bigalke H., et al., *Botulinum A Neurotoxin Inhibits Non-Cholinergic Synaptic Transmission in Mouse Spinal Cord Neurons in Culture*, Brain Research 360;318–324:1985; Habermann E., *Inhibition by Tetanus and Botulinum A Toxin of the release of [$^3H$]Noradrenaline and [$^3H$]GABA From Rat Brain Homogenate*, Experientia 44;224–226:1988, Bigalke H., et al.,

*Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244–251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline *botulinum* toxin type A, as set forth in Shantz, E. J., et al, *Properties and use of Botulinum toxin and Other Microbial Neurotoxins in Medicine*, Microbiol Rev. 56;80–99:1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of 1–2'$10^8$ $LD_{50}$ U/mg or greater; purified *botulinum* toxin type B with an approximately 156 kD molecular weight with a specific potency of 1–2×$10^8$ $LD_{50}$ U/mg or greater, and; purified *botulinum* toxin type F with an approximately 155 kD molecular weight with a specific potency of 1–2×$10^7$ $LD_{50}$ U/mg or greater.

Botulinum toxins and/or *botulinum* toxin complexes can be obtained from List Biological Laboratories, Inc., Campbell, Calif.; the Centre for Applied Microbiology and Research, Porton Down , U.K.; Wako (Osaka, Japan), Metabiologics (Madison, Wis.) as well as from Sigma Chemicals of St Louis, Mo. Pure *botulinum* toxin can also be used to prepare a pharmaceutical composition.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249–53:1997.

It has been reported that *botulinum* toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patients with Parkinson's disease, although it has been reported that results have not been impressive. Marjama-Jyons, J., et al., *Tremor-Predominant Parkinson's Disease*, Drugs & Aging 16(4) ;273–278:2000.

It is known that *botulinum* toxin type A can have an efficacy for up to 12 months (European *J. Neurology* 6 (Supp 4): S111–S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996;114(3):507, and *The Laryngoscope* 109:1344–1346:1999. However, the usual duration of an intramuscular injection of Botox® is typically about 3 to 4 months.

The success of *botulinum* toxin type A to treat a variety of clinical conditions has led to interest in other *botulinum* toxin serotypes. Two commercially available *botulinum* type A preparations for use in humans are BOTOX® available from Allergan, Inc., of Irvine, Calif., and Dysport® available from Beaufour Ipsen, Porton Down, England. A *Botulinum* toxin type B preparation (MyoBloc®) is available from Elan Pharmaceuticals of San Francisco, Calif.

In addition to having pharmacologic actions at the peripheral location, *botulinum* toxins may also have inhibitory effects in the central nervous system. Work by Weigand et al, *Nauny-Schmiedeberg's Arch. Pharmacol.* 1976; 292, 161–165, and Habermann, *Nauny-Schmiedeberg's Arch. Pharmacol.* 1974; 281, 47–56 showed that *botulinum* toxin is able to ascend to the spinal area by retrograde transport. As such, a *botulinum* toxin injected at a peripheral location, for example intramuscularly, may be retrograde transported to the spinal cord.

U.S. Pat. No. 5,989,545 discloses that a modified clostridial neurotoxin or fragment thereof, preferably a *botulinum* toxin, chemically conjugated or recombinantly fused to a particular targeting moiety can be used to treat pain by administration of the agent to the spinal cord.

A *botulinum* toxin has also been proposed for the treatment of rhinorrhea (chronic discharge from the nasal mucous membranes, i.e. runny nose), rhinitis (inflammation of the nasal mucous membranes), hyperhydrosis and other disorders mediated by the autonomic nervous system (U.S. Pat. No. 5,766,605), tension headache, (U.S. Pat. No. 6,458,365), migraine headache (U.S. Pat. No. 5,714,468), post-operative pain and visceral pain (U.S. Pat. No. 6,464,986), pain treatment by intraspinal toxin administration (U.S. Pat. No. 6,113,915), Parkinson's disease and other diseases with a motor disorder component, by intracranial toxin administration (U.S. Pat. No. 6,306,403), hair growth and hair retention (U.S. Pat. No. 6,299,893), psoriasis and dermatitis (U.S. Pat. No. 5,670,484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a *botulinum* toxin into the upper and lower esophageal, pyloric and anal sphincters)), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977) and neurogenic inflammation (U.S. Pat. No. 6,063,768). Additionally, controlled release toxin implants are known (see e.g. U.S. Pat. Nos. 6,306,423 and 6,312,708).

Tetanus toxin, as wells as derivatives (i.e. with a non-native targeting moiety), fragments, hybrids and chimeras thereof can also have therapeutic utility. The tetanus toxin bears many similarities to the *botulinum* toxins. Thus, both the tetanus toxin and the *botulinum* toxins are polypeptides made by closely related species of *Clostridium* (*Clostridium tetani* and *Clostridium botulinum*, respectively). Additionally, both the tetanus toxin and the *botulinum* toxins are dichain proteins composed of a light chain (molecular weight about 50 kD) covalently bound by a single disulfide bond to a heavy chain (molecular weight about 100 kD). Hence, the molecular weight of tetanus toxin and of each of the seven *botulinum* toxins (non-complexed) is about 150 kD. Furthermore, for both the tetanus toxin and the *botulinum* toxins, the light chain bears the domain which exhibits intracellular biological (protease) activity, while the heavy chain comprises the receptor binding (immunogenic) and cell membrane translocational domains.

Further, both the tetanus toxin and the *botulinum* toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of *botulinum* toxin by peripheral cholinergic neurons results in little if any retrograde transport, inhibition of acetylcholine exocytosis from the intoxicated peripheral motor neurons and a flaccid paralysis.

Finally, the tetanus toxin and the *botulinum* toxins resemble each other in both biosynthesis and molecular architecture. Thus, there is an overall 34% identity between the protein sequences of tetanus toxin and *botulinum* toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153–9158:1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is an effective method for treating sinus headache.

SUMMARY

The present invention meets this need and provides methods for effectively treating a sinus headache by local administration of a *Clostridial* toxin.

A method according to my invention can be carried out by administration of a *Clostridial* toxin to a patient with a sinus headache.

The *Clostridial* toxin used is preferably a *botulinum* toxin (as either a complex or as a pure [i.e. about 150 kDa molecule], such as a *botulinum* toxin A, B, C, D, E, F or G. Administration of the *Clostridial* toxin can be by a transdermal route (i.e. by application of a *Clostridial* toxin in a cream, patch or lotion vehicle), subdermal route (i.e. subcutaneous or intramuscular), intradermal, or into a sinus cavity route of administration.

A hypothesized physiological reason for the efficacy of my invention, as explained in greater detail below, is to reduce, inhibit or eliminate sensory input (afferent) from the periphery into the central nervous system (including to the brain) which is perceived by the patient as pain. Such pain sensory input can be attenuated or eliminated by targeting subdermal sensory neurons with a low dose of a *Clostridial* toxin.

The dose of a *Clostridial* toxin used according to the present invention is less than the amount of toxin that would be used to paralyze a muscle, since the intent of a method according to the present invention is not to paralyze a muscle but to reduce a pain sensory output from sensory neurons located in or on a muscle, or in or under the skin or in the vicinity of a sinus cavity.

An alternate physiological basis for the efficacy of my invention can be by reduction of inflammation of a sinus membrane by the administered *Clostridial* toxin. Thus, my invention can be practised by administering a *Clostridial* toxin to or to the vicinity of a sinus cavity. Alternately my invention can be practised by administering a *Clostridial* toxin to an intradermal, subdermal, intramuscular or para sinus cavity sensory (pain) neurons which generates the pain sensation.

The following definitions apply herein:

"About" means approximately or nearly and in the context of a numerical value or range set forth herein means ±10% of the numerical value or range recited or claimed.

"Alleviating" means a reduction in the occurrence of a sinus headache pain. Thus, alleviating includes some reduction, significant reduction, near total reduction, and total reduction of the sinus headache pain. An alleviating effect may not appear clinically for between 1 to 7 days after administration of a *Clostridial* toxin to a patient.

"*Botulinum* toxin" means a *botulinum* neurotoxin as either pure toxin or complex, and excludes *botulinum* toxins which are not neurotoxins such as the cytotoxic *botulinum* toxins $C_2$ and $C_3$.

"Local administration" means administration (i.e. by a subcutaneous, intramuscular, subdermal or transdermal route) of a pharmaceutical agent to or to the vicinity of a muscle or sinus cavity or of a subdermal location or in the head of a patient by a non-systemic route. Thus, local administration excludes systemic (i.e. to the blood circulation system) routes of administration, such as intravenous or oral administration. Peripheral administration means administration to the periphery (i.e. to a location on or within a limb, trunk or head of a patient) as opposed to a visceral or gut (i.e. to the viscera) administration.

"Treating" means to alleviate (or to eliminate) at least one symptom of a sinus headache, either temporarily or permanently.

The *Clostridial* neurotoxin is administered in a therapeutically effective amount to alleviate the pain of a sinus headache. A suitable *Clostridial* neurotoxin may be a neurotoxin made by a bacterium, for example, the neurotoxin may be made from a *Clostridium botulinum, Clostridium butyricum*, or *Clostridium beratti*. In certain embodiments of the invention, the sinus headache can be treated by intramuscular (facial) administration a *botulinum* toxin to the patient. The *botulinum* toxin may be a *botulinum* toxin type A, type B, type $C_1$, type D, type E, type F, or type G. The pain alleviating effects of the *botulinum* toxin may persist for between about 1 month and 5 years. The *botulinum* neurotoxin can be a recombinantly made *botulinum* neurotoxins, such as *botulinum* toxins produced by *E. coli*. In addition or alternatively, the *botulinum* neurotoxin can be a modified neurotroxin, that is a *botulinum* neurotoxin which has at least one of its amino acids deleted, modified or replaced, as compared to a native or the modified *botulinum* neurotoxin can be a recombinant produced *botulinum* neurotoxin or a derivative or fragment thereof.

A method for treating a sinus headache according to the present invention can comprise the step of local administration of a *botulinum* toxin to a patient with a sinus headache to thereby alleviate the sinus headache. The *botulinum* toxin can be selected from the group consisting of *botulinum* toxin types A, B, C, D, E, F and G. *Botulinum* toxin type A is a preferred *botulinum* toxin. The *botulinum* toxin can be administered in an amount of between about 1 unit and about 3,000 units and the alleviation of the sinus headache can persist for between about 1 month and about 5 years. The local administration of the *botulinum* toxin can be to or to a vicinity of a sinus cavity. Alternately, the local administration can be by intramuscular injection or to a subdermal location from which the patient perceives the existence of a sinus headache pain to arise, typically at the forehead.

A detailed embodiment of my invention can comprise a method for treating a sinus headache, the method comprising a step of local administration to a patient with a sinus headache of between about 1 unit and about 3,000 units of a *botulinum* toxin (for example between about 1–50 units of a *botulinum* toxin type A or between about 50 to 3,000 units of a *botulinum* toxin type B), thereby alleviating the sinus headache for between about 1 month and about 5 years.

DRAWINGS

The following drawings are presented to assist understanding of aspects and features of the present invention.

DESCRIPTION

Figure 1:
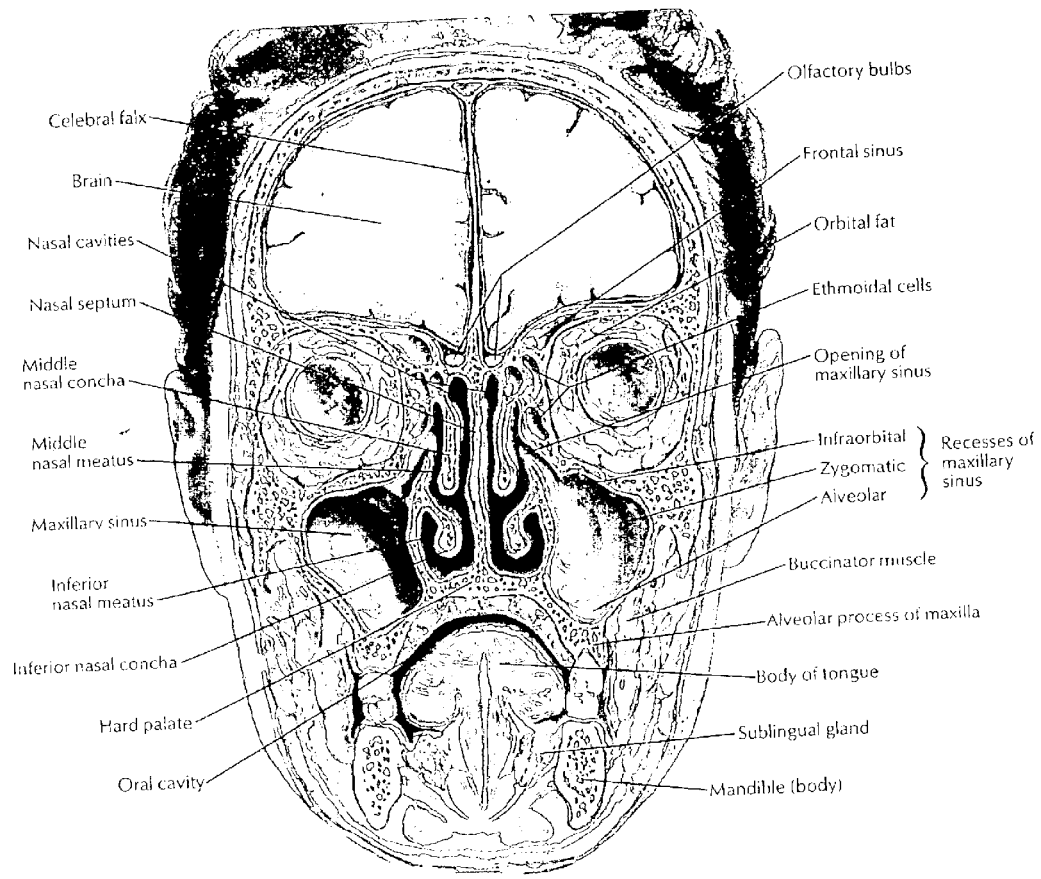
FIG. 1 is a coronal (front) cross sectional view of a human head illustrating the location of the paranasal sinuses.

The present invention is based on the discovery that a sinus headache can be treated by local administration of a therapeutically effective amount of a *botulinum* toxin. Thus, a *botulinum* toxin (such as a *botulinum* toxin serotype A, B, $C_1$, D, E, F or G) can be injected into or in the vicinity of a sinus cavity of a patient with a sinus headache to thereby suppress pain and/or treat the inflammation which can be a causative factor of the sinus headache. Alternately, the *botulinum* toxin can be administered to an intradermal or subdermal pain sensory neuron thereby suppressing and treating such a sinus headache.

It is known that a *botulinum* toxin can inhibit an excessive glandular secretion, as in the treatment of hyperhydrosis. It can be hypothesized is that administration of a *botulinum* toxin (as by injection to an intrasinus location) can act to reduce both the inflammation of the sinus to and the excess secretion by a sinus gland, thereby alleviating the pain of a sinus headache.

My invention is preferably practised by administering a *botulinum* toxin directly to one of the paranasal sinuses that is, to one or more of the paired frontal, ethmoidal, sphenoidal and/or maxillary sinuses. The paranasal sinuses are paired air-filled cavities in the bones of the face lined with mucous membranes. Excluded from the scope of the present invention is administration of a *botulinum* toxin to a nasal cavity (including to the nasal vestibule, turbinate, or nasal meatus), as can be carried out to treat rhinorrhea or rhinitis, because it is highly desirable for the efficacious practice of a method according to the present invention to apply the *botulinum* toxin directly to a sinus cavity tissue from which afferent pain signals are emanating and/or which bear an inflamed sinus membrane. It is important to note that the nasal passages (i.e. the nasal vestibule, turbinate, or nasal meatus) are distinct from the sinus cavities so that application of a *botulinum* toxin to a nasal passage or nasal cavity to treat rhinitis or rhinorrhea does this cause that the *botulinum* toxin has also be applied to a sinus cavity, and vice versa, due to the anatomical location of the nasal cavities vs. the paranasal sinuses. An alternate preferred method for practicing the present invention is by pericranial administration of a *botulinum* toxin to a patient with a sinus headache, as by intramuscular injection of the *botulinum* toxin into the glabellar, frontalis and/or temporalis muscles of a patient with a sinus headache.

Without wishing to be bound by theory a physiological mechanism can be proposed for the efficacy of the present invention. It is known that muscles have a complex system of innervation and sensory output. Thus, anterior motor neurons located in each segment of the anterior homs of the spinal cord gray matter give rise to efferent alpha motor neurons and efferent gamma motor neurons that leave the spinal cord by way of the anterior roots to innervate skeletal (extrafusal) muscle fibers. The alpha motor neurons cause contraction of extrafusal skeletal muscle fibers while the gamma motor neurons innervate the intrafusal fibers of skeletal muscle. As well as excitation by these two type of efferent anterior motor neuron projections, there are additional, afferent sensory neurons which project from muscle spindle and golgi tendon organs and act to transmit information regarding various muscle parameter status to the spinal cord, cerebellum and cerebral cortex. These afferent motor neurons which relay sensory information from the muscle spindle include type Ia and type II sensory afferent neurons. See e.g. pages 686–688 of Guyton A. C. et al., *Textbook of Medical Physiology*, W. B. Saunders Company 1996, ninth edition.

Significantly, it has been determined that a *botulinum* toxin can act to reduce transmission of sensory information from muscle type la afferent neurons. Aoki, K., *Physiology and pharmacology of therapeutic botulinum neurotoxins*, in Kreyden, O., editor, Hyperhydrosis and *botulinum* toxin in dermatology, Basel, Karger; 2002; 30: pages 107–116, at 109–110. And it has been hypothesized that *botulinum* toxin can have a direct effect upon muscle cell sensory afferents and modify signals from these afferents to the central nervous system. See e.g. Brin, M., et al., *Botulinum toxin type A: pharmacology*, in Mayer N., editor, Spasticity: etiology, evaluation, management and the role of *botulinum* toxin, 2002; pages 110–124, at 112–113; Cui, M., et al., *Mechanisms of the antinociceptive effect of subcutaneous BOTOX®: inhibition of peripheral and central nociceptive processing*, Naunyn Schmiedebergs Arch Pharmacol 2002; 365 (supp 2): R17; Aoki, K., et al., *Botulinum toxin type A and other botulinum toxin serotypes: a comparative review of biochemical and pharmacological actions*, Eur J. Neurol 2001: (suppl 5); 21–29. Thus, it has been demonstrated that *botulinum* toxin can cause an altered sensory output from muscle to CNS and brain.

Importantly, the sensory neurons from which afferent output is to be inhibited by a method according to the present invention need not be located on or within a muscle, but can be in an intradermal or subdermal location.

It can be postulated that the pain of a sinus headache is due to sensory (pain) input from afferent facial area neurons. Administration of a *botulinum* toxin to a facial muscles or skin to reduce sensory output from the muscle can result in alleviation of a sinus headache pain.

It is my hypothesis, as may be the case in the treatment of a migraine headache with a *botulinum* toxin, that signals transmitted by afferent pain nerves in or on muscle tissue (i.e. muscle spindle fibers and muscle pain fibers) or as a part of sensory structures in the skin or subdermally induce the pain sensation of a sinus headache. That is, afferent signal from muscles or skin structures provide sensory information to the brain which then leads to the generation of pain. Thus, a local administration of a *botulinum* toxin to muscle spindle fibers, pain fibers or other sensors in or in the vicinity of a muscle can act to alter the neural. signal afferent output from these muscles to the brain and thereby decrease the sensation of pain.

Important elements of my invention are firstly that is practised by use of a local administration of low dose of a *botulinum* toxin. The selected low dose does not cause a muscle paralysis. Secondly, the invention is practised by local administration of the low dose of the *botulinum* toxin to the muscle or to the muscle group which initiates the pain sensation or to a sinus membrane which is inflamed or from which a pain signal is generated.

The amount of the *Clostridial* toxin administered according to a method within the scope of the disclosed invention can vary according to the particular characteristics of the sinus headache being treated, including its severity and other various patient variables including size, weight, age, and responsiveness to therapy. To guide the practitioner, typically, no less than about 1 unit and no more than about 25 units of a *botulinum* toxin type A (such as BOTOX®) is administered per injection site (i.e. to each muscle portion injected), per patent treatment session. For a *botulinum* toxin type A such as DYSPORT®, no less than about 2 units and no more about 125 units of the *botulinum* toxin type A are administered per injection site, per patent treatment session. For a *botulinum* toxin type B such as MYOBLOC®, no less than about 40 units and no more about 1500 units of the *botulinum* toxin type B are administered per injection site, per patent treatment session. Less than about 1, 2 or 40 units (of BOTOX®, DYSPORT® and MYOBLOC® respectively) can fail to achieve a desired therapeutic effect, while more than about 25, 125 or 1500 units (of BOTOX®, DYSPORT® and MYOBLOC® respectively) can result in significant muscle hypotonicity, weakness and/or paralysis.

More preferably: for BOTOX® no less than about 2 units and no more about 20 units of a *botulinum* toxin type A; for DYSPORT® no less than about 4 units and no more than about 100 units, and; for MYOBLOC®, no less than about 80 units and no more than about 1000 units are, respectively, administered per injection site, per patent treatment session.

Most preferably: for BOTOX® no less than about 5 units and no more about 15 units of a *botulinum* toxin type A; for DYSPORT® no less than about 20 units and no more than about 75 units, and; for MYOBLOC®, no less than about 200 units and no more than about 750 units are, respectively, administered per injection site, per patent treatment session. It is important to note that there can be multiple injection sites (i.e. a pattern of injections) for each patient treatment session.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill). For example, the route and dosage for administration of a neurotoxin according to the present disclosed invention can be selected based upon criteria such as the solubility characteristics of the neurotoxin chosen as well as the intensity of pain perceived.

The present invention is based on the discovery that local administration of a *Clostridial* toxin can provide significant and long lasting relief from a sinus headache. The *Clostridial* toxins used in accordance with the invention disclosed herein can inhibit transmission of chemical or electrical signals between select neuronal groups that are involved in generation of a sinus headache pain. The *Clostridial* toxins preferably are not cytotoxic to the cells that are exposed to the *Clostridial* toxin. The *Clostridial* toxin can inhibit neurotransmission by reducing or preventing exocytosis of neurotransmitter from the neurons exposed to the *Clostridial* toxin. Or the applied *Clostridial* toxin can reduce neurotransmission by inhibiting the generation of action potentials of the neurons exposed to the toxin. The sinus headache pain alleviation effect provided by the *Clostridial* toxin can persist for a relatively long period of time, for example, for more than two months, and potentially for several years.

Examples of *Clostridial* toxins within the scope of the present invention include neurotoxins made by *Clostridium botulinum, Clostridium butyricum* and *Clostridium beratti* species. In addition, the botulinum toxins used in the methods of the invention may be a botulinum toxin selected from a group of botulinum toxin types A, B, C, D, E, F, and G. In one embodiment of the invention, the botulinum neurotoxin administered to the patient is botulinum toxin type A. Botulinum toxin type A is desirable due to its high potency in humans, ready availability, and known use for the treatment of skeletal and smooth muscle disorders when locally administered by intramuscular injection. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition may only contain a single type of neurotoxin, such as botulinum toxin type A, as the active ingredient to suppress neurotransmission, other therapeutic compositions may include two or more types of neurotoxins, which may provide enhanced therapeutic treatment of a sinus headache. For example, a composition administered to a patient may include botulinum toxin type A and botulinum toxin type B. Administering a single composition containing two different neurotoxins may permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat a sinus headache can include one or more neurotoxins, such as botulinum toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a botulinum toxin within a tissue appears to be a function of dose and can be graduated. Jankovic J., et al Therapy With Botulinum Toxin, Marcel Dekker, Inc., (1994), page 150. Thus, diffusion of botulinum toxin can be controlled to reduce potentially undesirable side effects that may affect the patient's cognitive abilities. For example, the neurotoxin can be administered so that the neurotoxin primarily effects neural systems believed to be involved in the generation of pain and/or inflammation in or in the vicinity of the sinus cavities, and does not have negatively adverse effects on other neural systems.

A polyanhydride polymer, Gliadel® (Stolle R & D, Inc., Cincinnati, Ohio) a copolymer of polycarboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum toil pouches under nitrogen atmosphere and sterilized by 2.2 megaRads of gamma irradiation. The polymer permits release of carmustine over a 2–3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345;1008–1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide* and *Paclitaxel From a Biodegradable Polymer Implant in the Monkey Brain*, Cancer Research 58;672–684:1998.

Local administration of a Clostridial toxin, such as a botulinum toxin, can provide a high, local therapeutic level of the toxin. A controlled release polymer capable of long term, local delivery of a *Clostridial* toxin to a target muscle permits effective dosing of a target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a *botulinum* toxin, according to the present invention, by injection or implant to a target tissue provides a superior alternative to systemic administration of pharmaceuticals to patients to alleviate the pain of a sinus headache.

The amount of a *Clostridial* toxin selected for local administration to a target tissue according to the present disclosed invention can be varied based upon criteria such as the severity of the sinus headache being treated, the extent of muscle tissue to be treated, solubility characteristics of the neurotoxin toxin chosen as well as the age, sex, weight and health of the patient. For example, the extent of the area of muscle tissue influenced is believed to be proportional to the volume of neurotoxin injected, while the quantity of the suppressant effect is, for most dose ranges, believed to be proportional to the concentration of a *Clostridial* toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

EXAMPLES

The following non-limiting examples provide those of ordinary skill in the art with specific preferred methods to treat conditions within the scope of the present invention and are not intended to limit the scope of the invention. In the following examples various modes of non-systemic administration of a *Clostridial* neurotoxin can be carried out. For example, by intramuscular injection, subcutaneous injection or by implantation of a controlled release implant.

Example 1

*Botulinum* Toxin Type A Therapy for a Sinus Headache

Figure 2:
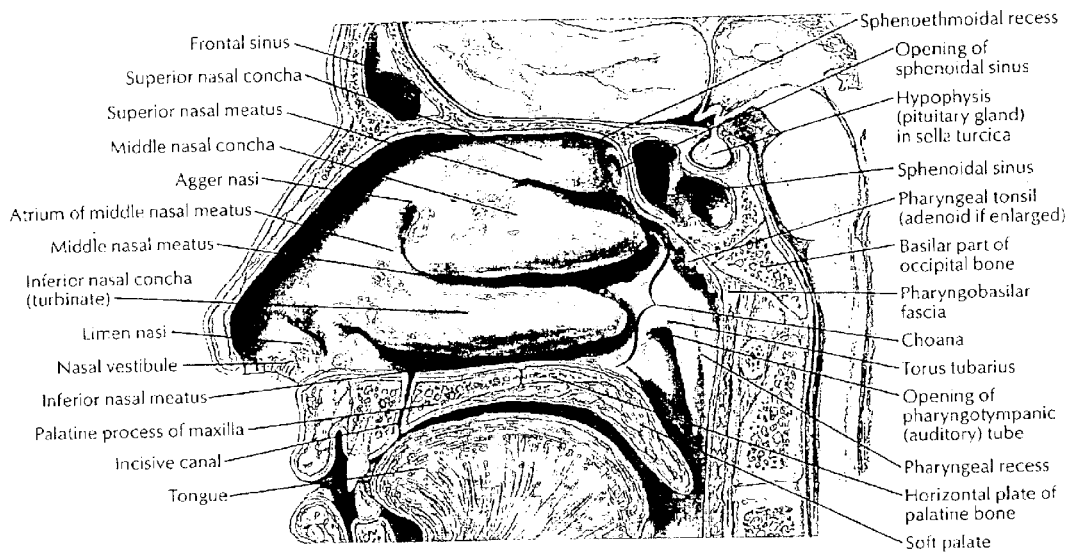
FIG. 2 is a side cross section view of a partial human head through the lateral wall of a nasal cavity.
Figure 3:
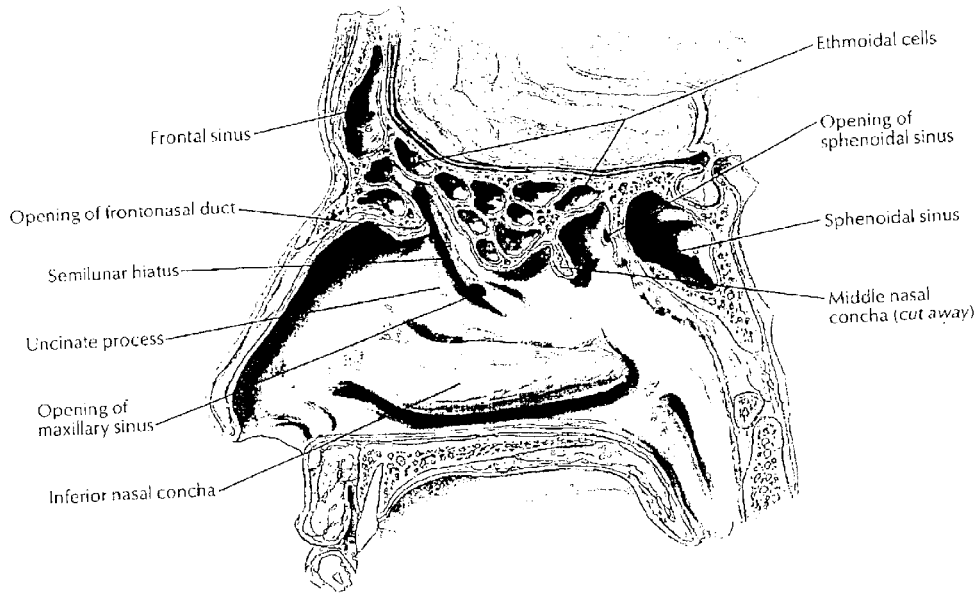
FIG. 3 is a partial sagittal (side) cross section view of a partial human head to illustrate the location of the paranasal sinuses.

A female patient, 32 years old, complains of pain in the area of the paranasal sinuses. The pain is described as pain is constant, even, and not throbbing. It is not associated with nausea, light, or noise sensitivity. Sinus headache is diagnosed and the patient is treated by injection of 10 units a *botulinum* toxin type A (i.e. BOTOX®) into each of the glabellar, frontalis and temporalis muscles (30 units total toxin). Alternately, about 10 units of the *botulinum* toxin type A can be injected directly into one or more of the sinuses (see FIGS. 1–3 for the disposition of the sinuses) at the location and on the side where the pain is reported to be most intense. Within 1–7 days after the *botulinum* toxin administration the patient reports complete alleviation of her sinus headache pain and the alleviation of her condition can persist for 4–6 months.

A *botulinum* toxin type B, C, D, E, F or G can be substituted for the *botulinum* toxin type A used above, for example by use of 250 units of a *botulinum* toxin type B.

Example 2

*Botulinum* Toxin Type B Therapy for a Sinus Headache

Figure 4:
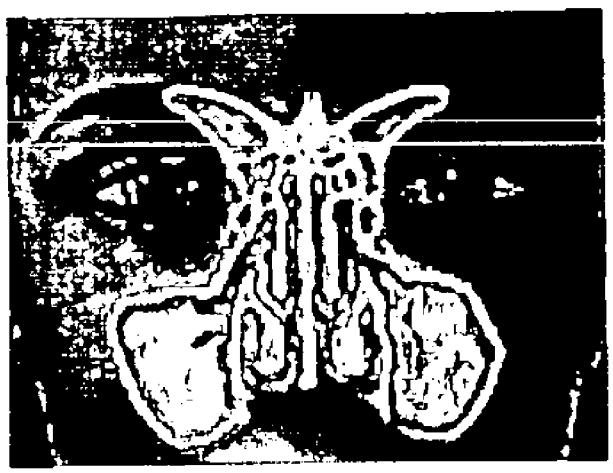
FIG. 4 is a frontal view of a partial human face with superimposed location of the sinuses and showing an infected left maxillary sinus.
Figure 5:
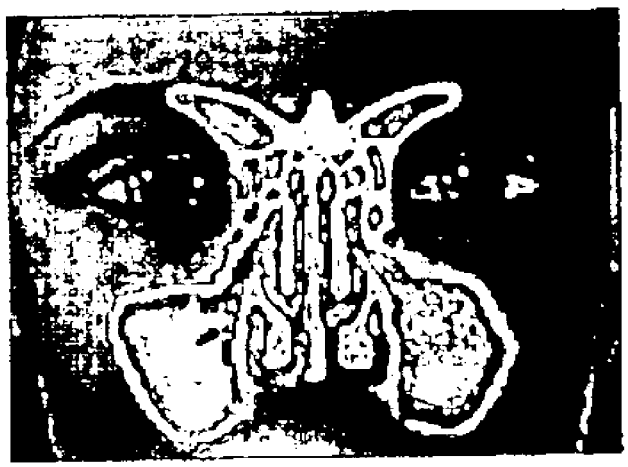
FIG. 5 is the FIG. 4 view showing in addition an inflamed mucus lining of the left maxillary sinus.

A male patient 28 years of age presents with a dull, deep pain in the front of his head and face. He reports exacerbation upon bending over down. There is a greenish nasal discharge, red and swollen nasal passages and a mild fever (101 degrees C.). The patient is treated by injection of 10 units a *botulinum* toxin type A (i.e. BOTOX®) into each of the sinus cavities. At least 10 units of the toxin can be injected into the infected left maxillary sinus. FIG. 4 illustrates an infected left maxillary sinus. If Inflammation is present an additional 5 units of the *botulinum* toxin can be administered. FIG. 5 illustrates a left maxillary sinus with an inflamed membrane. Within 1–7 days after toxin administration the patient reports complete alleviation of his sinus headache and the alleviation of his condition can persist for 4–6 months.

In both Examples 1 and 2, the *botulinum* toxin can be administered by an endoscopic sinus procedure as set forth for example in Anderson, T., et al., *Surgical intervention for sinusitis in adults*, Curr Allergy Asthma Rep 2001 May;1 (3):282–8 using the endoscopic injection instrument described in U.S. Pat. Nos. 5,437,291 and 5,674,205.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a sinus headache pain wherein two or more neurotoxins, such as two or more *botulinum* toxins, are administered concurrently or consecutively. For example, *botulinum* toxin type A can be administered until a loss of clinical response or neutralizing antibodies develop, followed by administration of *botulinum* toxin type B. Alternately, a combination of any two or more of the *botulinum* serotypes A–G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a *botulinum* toxin, begins to exert its therapeutic effect.

A method for treating a disorder according to the invention disclosed herein has many benefits and advantages, including the following:

1. the symptoms of a sinus headache can be dramatically reduced or eliminated.

2. the symptoms of a sinus headache can be reduced or eliminated for at least about two to about six months per injection of neurotoxin and for from about one year to about five years upon use of a controlled release neurotoxin implant.

3. the injected or implanted *Clostridial* neurotoxin shows little or no tendency to diffuse or to be transported away from the intramuscular (or intradermal or subdermal) injection or implantation site.

4. few or no significant undesirable side effects occur from intramuscular (or intradermal or subdermal) injection or implantation of the *Clostridial* neurotoxin.

5. the present methods can result in the desirable side effects of greater patient mobility, a more positive attitude, and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods wherein two or more *Clostridial* neurotoxins, such as two or more *botulinum* toxins, are administered concurrently or consecutively. For example, *botulinum* toxin type A can be locally administered until a loss of clinical response or neutralizing antibodies develop, followed by administration of *botulinum* toxin type B. Furthermore, non-neurotoxin compounds can be locally administered prior to, concurrently with or subsequent to administration of the neurotoxin to provide adjunct effect such as enhanced or a more rapid onset of pain suppression before the neurotoxin, such as a *botulinum* toxin, begins to exert its more long lasting pain suppressant effect.

My invention also includes within its scope the use of a neurotoxin, such as a *botulinum* toxin, in the preparation of a medicament for the treatment of an obsessive-compulsive disorder, by local administration of the *Clostridial* neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating a sinus headache, the method comprising a step of local administration of a *botulinum* toxin to a patient with a sinus headache, thereby treating a sinus headache, wherein the local administration of the *botulinum* toxin is to a facial muscle of the patient.

2. The method of claim 1, wherein the *botulinum* toxin is selected from the group consisting of *botulinum* toxin types A, B, C, D, E, F and G.

3. The method of claim 1, wherein the *botulinum* toxin is a *botulinum* toxin type A.

4. The method of claim 1, wherein the *botulinum* toxin is administered in an amount of between about 1 unit and about 3,000 units.

5. A method for treating a sinus headache, the method comprising a step of local administration of a *botulinum* toxin to a patient with a sinus headache, thereby treating a sinus headache, wherein the local administration is to a paranasal sinus cavity membrane of the patient.

6. The method of claim 5, wherein the *botulinum* toxin is selected from the group consisting of *botulinum* toxin types A, B, C, D, E, F and G.

7. The method of claim 5, wherein the *botulinum* toxin is a *botulinum* toxin type A.

8. The method of claim 5, wherein the *botulinum* toxin is administered in an amount of between about 1 unit and about 3,000 units.

9. A method for treating a sinus headache, the method comprising a step of local administration of a *botulinum* toxin to a patient with a sinus headache, thereby treating a sinus headache, wherein the local administration is to the forehead of the patient.

10. The method of claim 9, wherein the *botulinum* toxin is selected from the group consisting of *botulinum* toxin types A, B, C, D, E, F and G.

11. The method of claim 9, wherein the *botulinum* toxin is a *botulinum* toxin type A.

12. The method of claim 9, wherein the *botulinum* toxin is administered in an amount of between about 1 unit and about 3,000 units.

13. A method for treating a sinus headache, the method comprising a step of local administration of a *botulinum* toxin to a patient with a sinus headache, thereby treating a sinus headache, wherein the local administration is by intramuscular or subcutaneous administration to a location on or within the head of the patient.

14. The method of claim 13, wherein the *botulinum* toxin is selected from the group consisting of *botulinum* toxin types A, B, C, D, E, F and G.

15. The method of claim 13, wherein the *botulinum* toxin is a *botulinum* toxin type A.

16. The method of claim 13, wherein the *botulinum* toxin is administered in an amount of between about 1 unit and about 3,000 units.

17. A method for treating a sinus headache, the method comprising a step of local administration of a *botulinum* toxin to a patient with a sinus headache, thereby treating a sinus headache, wherein the local administration of the *botulinum* toxin is to a subdermal location or to a muscle location on or within the head of the patient from which the patient perceives the sinus headache pain to arise.

18. The method of claim 17, wherein the *botulinum* toxin is selected from the group consisting of botulinum toxin types A, B, C, D, E, F and G.

19. The method of claim 17, wherein the *botulinum* toxin is a *botulinum* toxin type A.

20. The method of claim 17, wherein the *botulinum* toxin is administered in an amount of between about 1 unit and about 3,000 units.

* * * * *